US012397095B2

United States Patent
Friederichs et al.

(10) Patent No.: US 12,397,095 B2
(45) Date of Patent: Aug. 26, 2025

(54) MEDICAMENT PREPARATION DEVICES, METHODS, AND SYSTEMS

(71) Applicant: NxStage Medical, Inc., Lawrence, MA (US)

(72) Inventors: Goetz Friederichs, Waltham, MA (US); Gregory Yantz, Waltham, MA (US)

(73) Assignee: NxStage Medical, Inc., Lawrence, MA (US)

( * ) Notice: Subject to any disclaimer, the term of this patent is extended or adjusted under 35 U.S.C. 154(b) by 784 days.

(21) Appl. No.: 17/696,546

(22) Filed: Mar. 16, 2022

(65) Prior Publication Data

US 2022/0296796 A1    Sep. 22, 2022

Related U.S. Application Data

(60) Provisional application No. 63/162,388, filed on Mar. 17, 2021.

(51) Int. Cl.
*A61M 1/16*    (2006.01)
*A61J 1/10*    (2006.01)
(Continued)

(52) U.S. Cl.
CPC ............... *A61M 1/287* (2013.01); *A61J 1/10* (2013.01); *A61J 3/00* (2013.01); *A61M 1/1601* (2014.02);
(Continued)

(58) Field of Classification Search
CPC .. A61M 1/1601; A61M 1/1656; A61M 1/287; A61M 60/279; A61M 2205/123;
(Continued)

(56) References Cited

U.S. PATENT DOCUMENTS 4,136,708 A    1/1979   Cosentino et al.
8,191,339 B2   6/2012   Tribble et al.
(Continued)

FOREIGN PATENT DOCUMENTS

EP      1312386 A2    5/2003
JP   2009533092 A    9/2009
(Continued)

OTHER PUBLICATIONS

International Search Report and Written Opinion mailed Jun. 14, 2022 for International Patent Application No. PCT/US2022/021477.

(Continued)

*Primary Examiner* — John Kim
(74) *Attorney, Agent, or Firm* — Potomac Law Group, PLLC

(57) ABSTRACT

A system for preparing a medicament for use by a medicament user includes a proportioning machine with a controller and pumping and clamping actuators to engage a fluid circuit having pumping and clamping portions that engage with respective actuators of the proportioning machine. The fluid circuit includes a mixing container that is initially empty and later filled with a concentrated medicament from a concentrate container. The proportioning machine is configured to receive purified water and to mix it with the concentrated medicament to produce a medicament and to output the medicament to a medicament consumer in such a way that to the medicament consumer the medicament appears to be provided from a bag of medicament.

10 Claims, 12 Drawing Sheets

(51) Int. Cl.
*A61J 3/00* (2006.01)
*A61M 1/28* (2006.01)
*A61M 60/279* (2021.01)
*C02F 1/00* (2023.01)

(52) U.S. Cl.
CPC ........ *A61M 1/1656* (2013.01); *A61M 60/279* (2021.01); *C02F 1/00* (2013.01); *A61M 2205/123* (2013.01); *A61M 2205/3317* (2013.01); *A61M 2205/3334* (2013.01); *A61M 2205/3337* (2013.01); *A61M 2209/04* (2013.01)

(58) Field of Classification Search
CPC .. A61M 2205/3317; A61M 2205/3334; A61M 2205/3337; A61M 2209/04; A61J 1/10; A61J 3/00; C02F 1/00
See application file for complete search history.

(56) References Cited

U.S. PATENT DOCUMENTS

| | | |
|---|---|---|
| 9,867,929 B2 | 1/2018 | Searle et al. |
| 11,207,454 B2 | 12/2021 | Wyeth et al. |
| 2015/0005699 A1 | 1/2015 | Burbank et al. |
| 2017/0290970 A1 | 10/2017 | Friederichs et al. |
| 2017/0319768 A1 | 11/2017 | Szpara et al. |
| 2018/0104400 A1 | 4/2018 | Burbank et al. |
| 2019/0151526 A1 | 5/2019 | Wieslander et al. |
| 2019/0217000 A1 | 7/2019 | Burbank et al. |
| 2019/0262522 A1 | 8/2019 | Wyeth et al. |
| 2019/0262524 A1 | 8/2019 | Wyeth et al. |
| 2019/0262526 A1 | 8/2019 | Wyeth et al. |
| 2020/0009308 A1 | 1/2020 | Friederichs et al. |
| 2020/0016317 A1 | 1/2020 | Kelly et al. |
| 2020/0171230 A1 | 6/2020 | Brugger et al. |
| 2020/0254167 A1 | 8/2020 | Rohde et al. |
| 2020/0390954 A1 | 12/2020 | Rovatti et al. |
| 2022/0126005 A1 | 4/2022 | Friederichs et al. |

FOREIGN PATENT DOCUMENTS

| | | |
|---|---|---|
| JP | 2018134444 A | 8/2018 |
| WO | 2013141896 A1 | 9/2013 |
| WO | 2020237033 A1 | 11/2020 |
| WO | 2021101899 A1 | 5/2021 |
| WO | 2022086922 A2 | 4/2022 |
| WO | 2022204253 A1 | 9/2022 |

OTHER PUBLICATIONS

International Search Report and Written Opinion mailed Jun. 3, 2022 for International Patent Application No. PCT/US2022/020331.
International Search Report and Written Opinion mailed Mar. 21, 2022 for International Patent Application No. PCT/US2021/055550.
Invitation to Pay Additional Fees mailed Apr. 29, 2022 for International Patent Application No. PCT/US2022/020583.
Invitation to Pay Additional Fees mailed Jun. 3, 2022 for International Patent Application No. PCT/US2022/022591.
Invitation to Pay Additional Fees mailed May 26, 2022 for International Patent Application No. PCT/US2022/021955.
Office Action (Communication Pursuant to Article 94(3) EPC) dated Apr. 19, 2024 for European Patent Application No. 21806560.5.
Extended European Search Report dated Jul. 8, 2024 for European Patent Application No. 22772141.2.
Partial Supplementary European Search Report dated Jul. 4, 2024 for European Patent Application No. 22772033.1.
Gotch et al., "Mechanisms determining the ratio of conductivity clearance to urea clearance," Kidney International, vol. 66, Supplement 8, Jul. 2004, pp. S-3-S-24.
International Search Report and Written Opinion mailed Aug. 1, 2022 for International Patent Application No. PCT/US2022/022591.
International Search Report and Written Opinion mailed Aug. 30, 2022 for International Patent Application No. PCT/US2022/020583.
International Search Report and Written Opinion mailed Jun. 24, 2022 for International Patent Application No. PCT/US2022/021501.
International Search Report and Written Opinion mailed Sep. 9, 2022 for International Application No. PCT/US2022/021955.
Extended European Search Report dated Feb. 4, 2025 for European Patent Application No. 22782109.7.
Office Action (Notice of Reasons for Refusal) mailed Apr. 22, 2025 for Japanese Patent Application No. 2023-523619.

MEDICAMENT PREPARATION DEVICES, METHODS, AND SYSTEMS

CROSS-REFERENCE TO RELATED APPLICATIONS

This application claims the benefit of U.S. Provisional Application No. 63/162,388 filed Mar. 17, 2021, which is incorporated herein by reference in its entirety.

BACKGROUND

The disclosed subject matter relates generally to devices, methods, systems, improvements, and components for preparing medicaments and making medicament available for use by a consumer, for example, a dialysis cycler.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal dialysis fluid is infused into a patient's peritoneal cavity using a catheter that has been inserted through the abdominal wall. The fluid remains in the peritoneal cavity for a dwell period. Osmotic exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysis fluid is removed from the body cavity through the catheter.

SUMMARY

Methods, device, and systems for preparing medicaments such as, but not limited to, dialysis fluid are disclosed. In embodiments, medicament is prepared at a point of care (POC) automatically using a daily sterile disposable fluid circuit, one or more concentrates to make batches of medicament at the POC. The dialysis fluid may be used at the POC for any type of renal replacement therapy, including at least peritoneal dialysis, hemodialysis, hemofiltration, and hemodiafiltration.

In embodiments, peritoneal dialysis fluid is prepared at a point of use automatically using a daily sterile disposable fluid circuit and one or more long-term concentrate containers that are changed only after multiple days (e.g. weekly). The daily disposable may have concentrate containers that are initially empty and are filled from the long-term concentrate containers once per day at the beginning of a treatment.

Embodiments of medicament preparation, devices, systems, and methods are described herein. The features, in some cases, relate to automated dialysis such as peritoneal dialysis, hemodialysis and others, and in particular to systems, methods, and devices that prepare peritoneal dialysis fluid in a safe and automated way at a point of care. The disclosed features may be applied to any kind of medicament system and are not limited to dialysis fluid.

In embodiments, a system that prepares a medical fluid is configured in such a manner that it outputs the medical fluid to a consuming process (for example, a peritoneal dialysis cycler) wherein the consuming process does not distinguish between the system that prepares the medical fluid and pre-packaged bags of dialysate. This allows embodiments of the presently disclosed system for preparing the medical fluid to be used with any type of a cycler, without any special customization or modification of the cycler.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
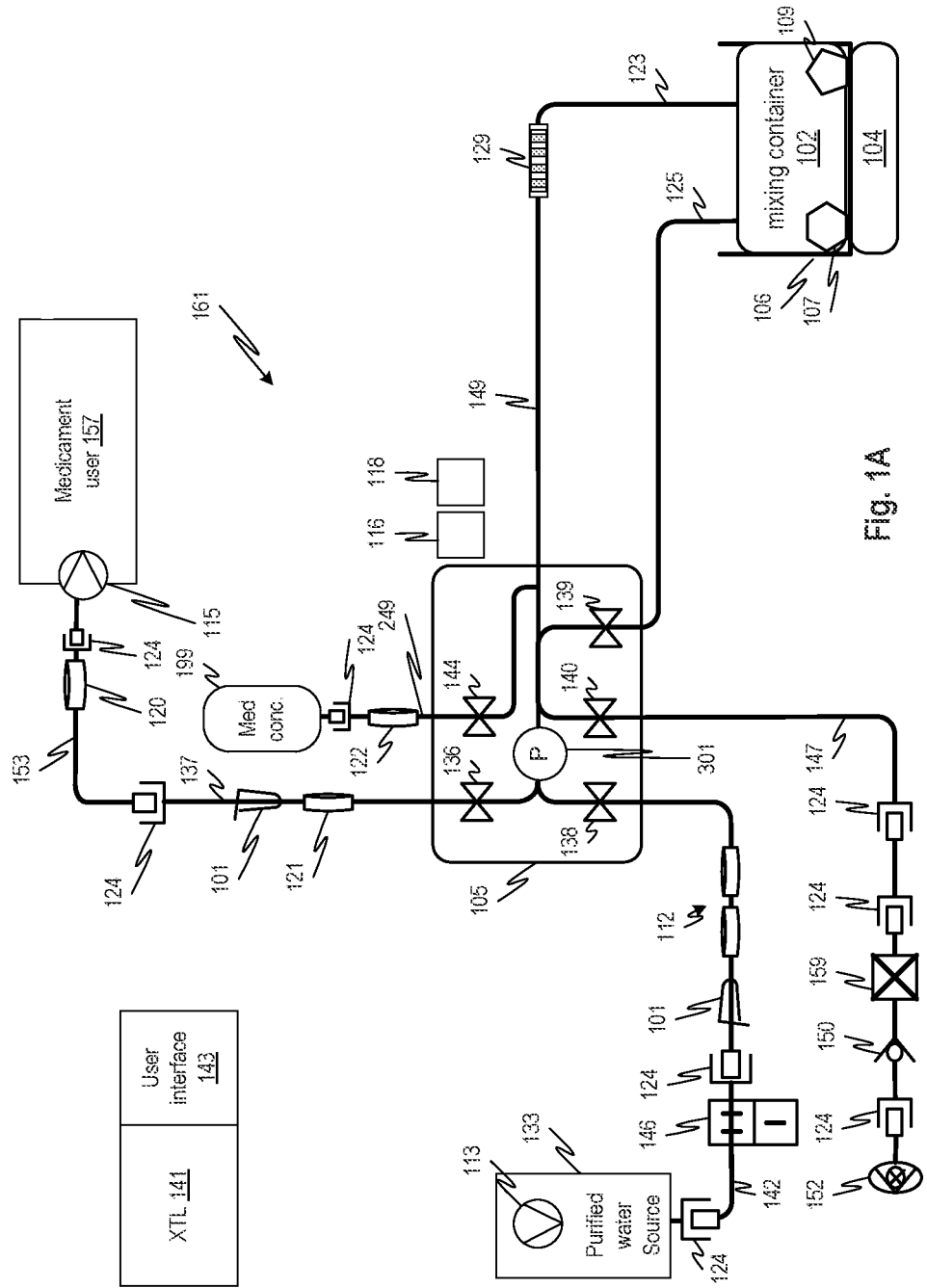
FIG. 1A shows a system for preparing a ready to use medicament from concentrated medicament and water according to embodiments of the disclosed subject matter.

FIG. 1A shows an embodiment of a system that uses water and concentrated medicament 199 (also referred to as "medicament concentrate" or "concentrate") to make a therapeutic fluid that can be used for treatment according to embodiments of the disclosed subject matter. In embodiments, the concentrated medicament may be a dextrose solution. Referring to FIG. 1A, a purified water source 133 with a water pump 113 supplies highly purified water through a connector 124 through a water line 142. The water line 142 has a non-reopenable clamp 146, another connector 124, a manual tube clamp 101, and a pair of redundant 0.2 micron sterilizing filters 112, as shown. In embodiments, different types of sterilizing filters may be used, and not limited to 0.2 micron, or to two redundant filters. For example, a single filter may be used and a testing protocol provided to ensure that the filter does not fail before replacement.

A water inlet clamp 138, batch release clamp 136, and a conductivity sensor clamp 140 are controlled by a controller 141, which may be operatively coupled to a user interface 143, which may include a visual and/or audible output and various devices for receiving user input. The controller 141 controls the pinch clamps and a peristaltic pump 129 to make a batch of diluted concentrate in a mixing container 102 by diluting medicament concentrate (e.g., dialysis fluid concentrate) in the mixing container 102. The mixing container 102 is supplied empty and permanently connected to a fluid circuit that includes fluid lines 149, 123, and 125.

A pressure sensor 301 is provided in the flow path as shown and outputs a signal representative of the pressure in the fluid lines that are fluidly connected to the pressure sensor. This pressure signal may be provided to controller 141.

In embodiments, the medicament concentrate 199 is provided in a separate package that is connected via connector 124 to concentrate line 249 as shown. The concentrate line 249 may include an optional filter 122. The filter 122 may be a touch contamination protection filter, such as a 0.2 micron filter.

The mixing container 102 may be a part of a disposable component 161 that is replaced regularly, such as with each batch, every day, every week, or every month. In an embodiment, the mixing container 102 is empty initially when the disposable component 161 is connected to the system.

The mixing container 102 may be made of a flexible material, such as a polymer so its shape is not rigid. To provide support for the mixing container 102, it is held by a tub 106 which is sufficiently rigid to support the mixing container 102 when it is full of fluid. A leak sensor 107 is provided in the tub 106 and it detects leaks into the tub 106 while a temperature sensor 109 may also be provided in or on the tub 106 and it detects the temperature of the fluid in the mixing container 102. A warmer 104 may be provided as shown to provide heat to tub 106, but the warmer 104 may be omitted if another heater exists elsewhere in the system. Note that the concentrate 199 that will be supplied to the mixing container 102 may be used for making any type of medicament, not just dialysis fluid.

To supply water to mixing container 102, clamp 139 can remain closed, and pump 129 runs to move the water from water line 142 to supply line 123 and mixing container 102 while valve 138 is open. Also, to make the medicament available to the medicament user 157, clamps 136 and 139 are opened and the other clamps are closed. There is no backpressure provided by a cracking check valve as in the embodiment of FIG. 1A. Thus, the medicament pump 115 may draw from the mixing container 102 without the assistance of a predefined backpressure, hence without the use of peristaltic pump 129. Alternatively, the peristaltic pump 129 may be run through a circulating path of 149, 123, and 125 with a feedback-controlled clamp 139 according to pressure indicated by pressure sensor 301. Here, clamps are closed except for 136 and 139 and the medicament user draws from a pressurized line.

Figure 1B:
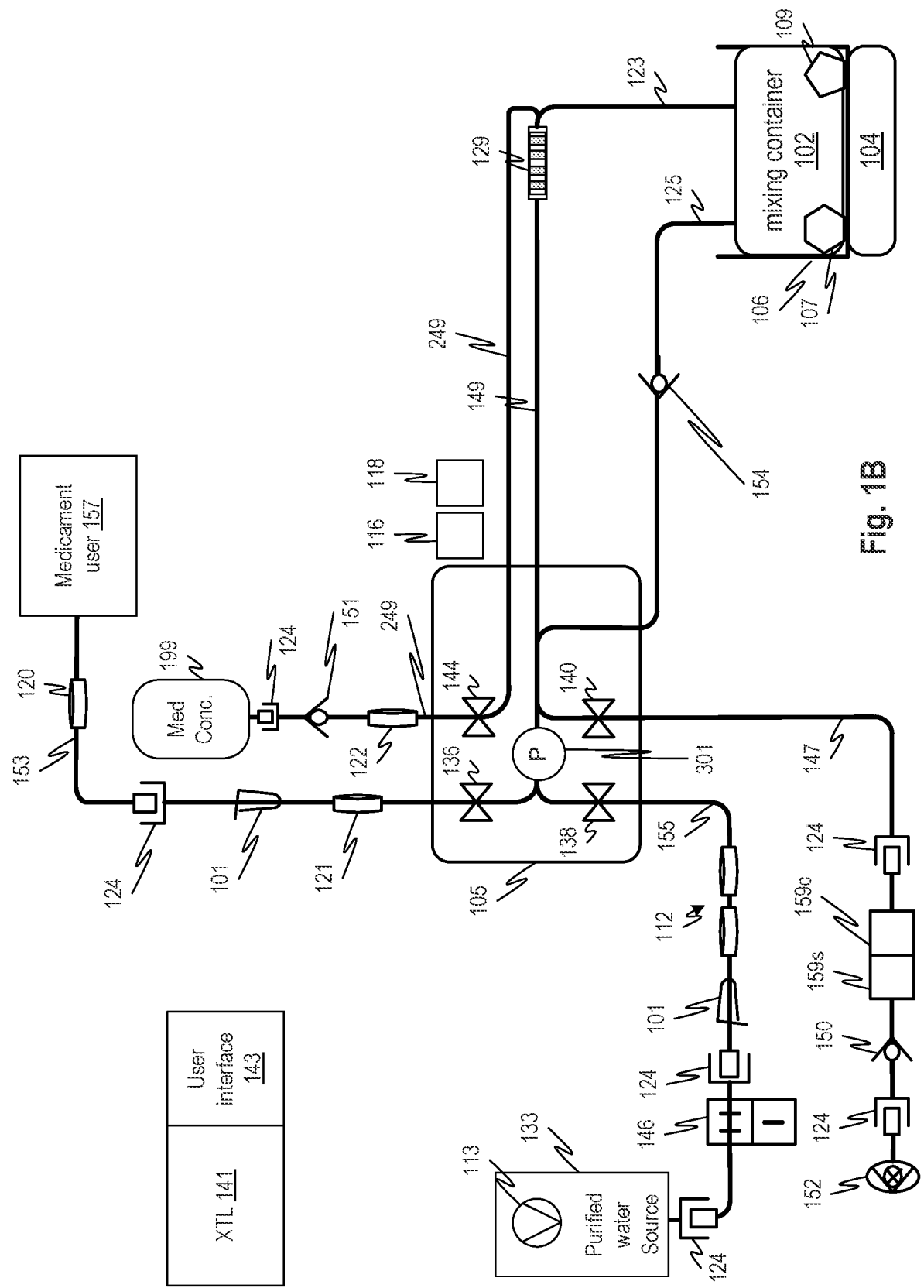
FIG. 1B shows another example of a system for preparing a ready to use medicament from concentrated medicament and water according to embodiments of the disclosed subject matter.

FIG. 1B shows a medicament generation system that is like that of FIG. 1A except that there is no valve 139 and instead cracking pressure check valve 154 is provided. The check valve 154 prevents flow in line 125 out of mixing container 102, and allows flow into mixing container 102 only when the cracking pressure is overcome. The cracking pressure may be selected at 3.5 PSI in embodiments.

Likewise, a check valve 151 may be added to the concentrate supply line 249 as shown, preventing back flow of concentrate into the container of concentrate 199. In embodiments, this allows for the safe preparation of multiple batches of diluted medicament from the same container of concentrate 199, as back flow (which is undesirable) into the concentrate container is prevented. In addition, the concentrate fill line 249 is routed to an opposite side of the peristaltic pump 129 as compared with FIG. 1A. In embodiments, the cracking pressure of check valve 151 is lower than the cracking pressure of check valve 154. When the peristaltic pump 129 rotates in a direction that draws concentrate from the container of concentrate 199, the difference in the cracking pressures helps ensure that contents of the mixing container 102 are not drawn out of the container when concentrate is being drawn through concentrate line 249.

Another difference with respect to FIG. 1A is the presence of two conductivity/temperature sensors 159$c$ and 159$s$, but it will be understood that the single conductivity/temperature sensor 159 in FIG. 1A can be replaced with two sensors as shown in FIG. 1B.

Note that in variations of most of the embodiments, the purified water source 133 may include a container or containers of purified water such as one or more polymer bags. In such embodiments, there may be a water pump arranged in a "pull" configuration. In any of the embodiments, the medicament user 157 may include a pump, such as the pump 115 illustrated in FIG. 1A. For example, the medicament user 157 may include a dialysis cycler that is configured to draw from a container of dialysis fluid.

To permit the medicament user 157 to draw medicament on-demand, the controller 141 may be programmed to maintain a constant pressure that is compatible with a pump in the medicament user 157. For example, the pressure-based control using the pressure sensor 301 may maintain a pressure that mimics a simple container that allows the medicament user 157 to draw from a container of dialysis fluid.

In embodiments, the medicament user 157 can use its own pump, such as the pump 115, to move fluid from the mixing container 102 without the use of pump 129. In this example, valves 136 and 139 will be opened, and the medicament user 157 will operate its pump to draw fluid form the mixing container 102.

Figure 1C:
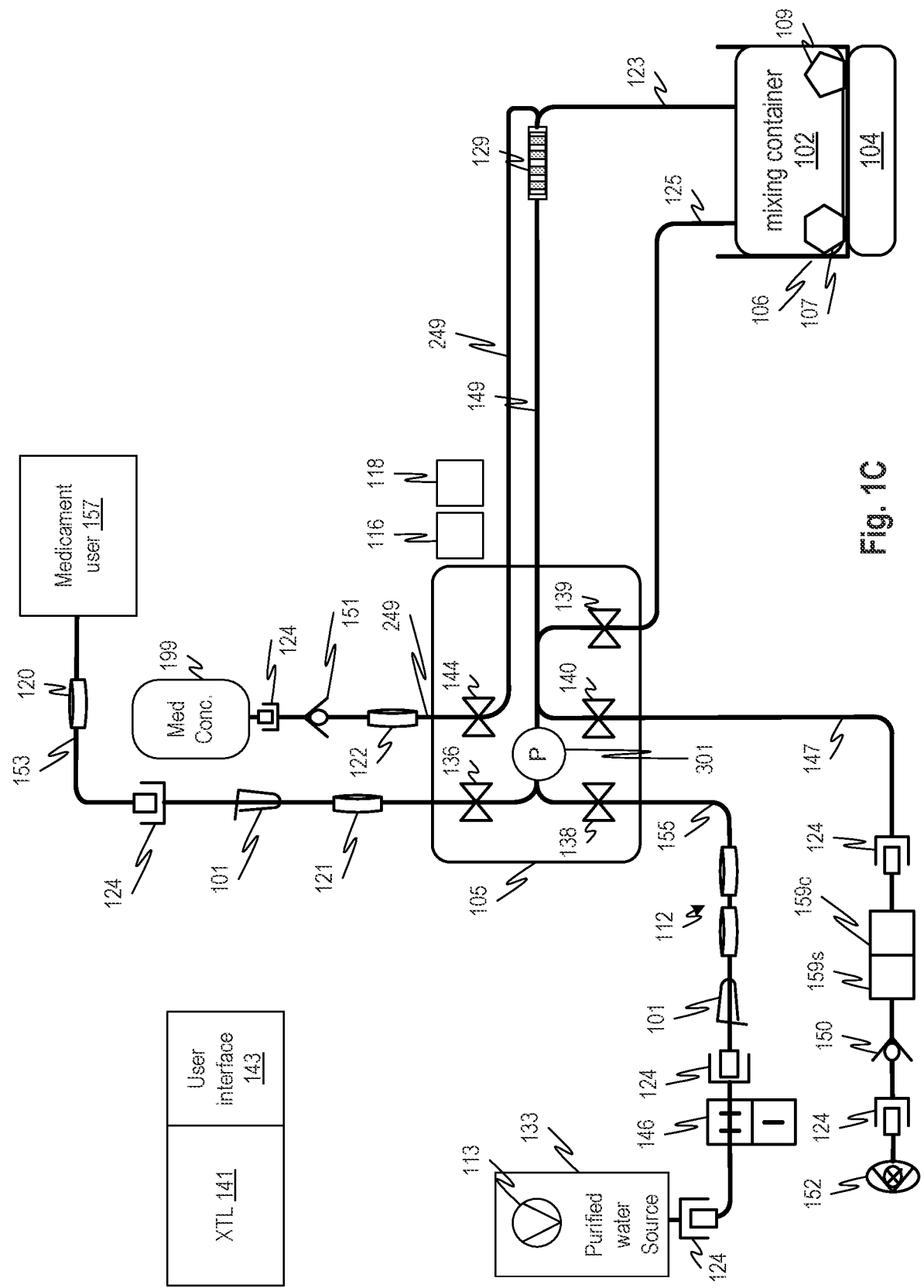
FIG. 1C shows another example of a system for preparing a ready to use medicament from concentrated medicament and water according to embodiments of the disclosed subject matter.

FIG. 1C shows another variation of a medicament generation system of FIG. 1B, except that cracking check valve 154 is replaced with valve 139. Similar to FIG. 1B, a check valve 151 may be added to the concentrate supply line 249 as shown, preventing back flow of concentrate into the container of concentrate 199. In embodiments, this allows for the safe preparation of multiple batches of diluted medicament from the same container of concentrate 199, as back flow (which is undesirable) into the concentrate container is prevented.

Figure 2A:
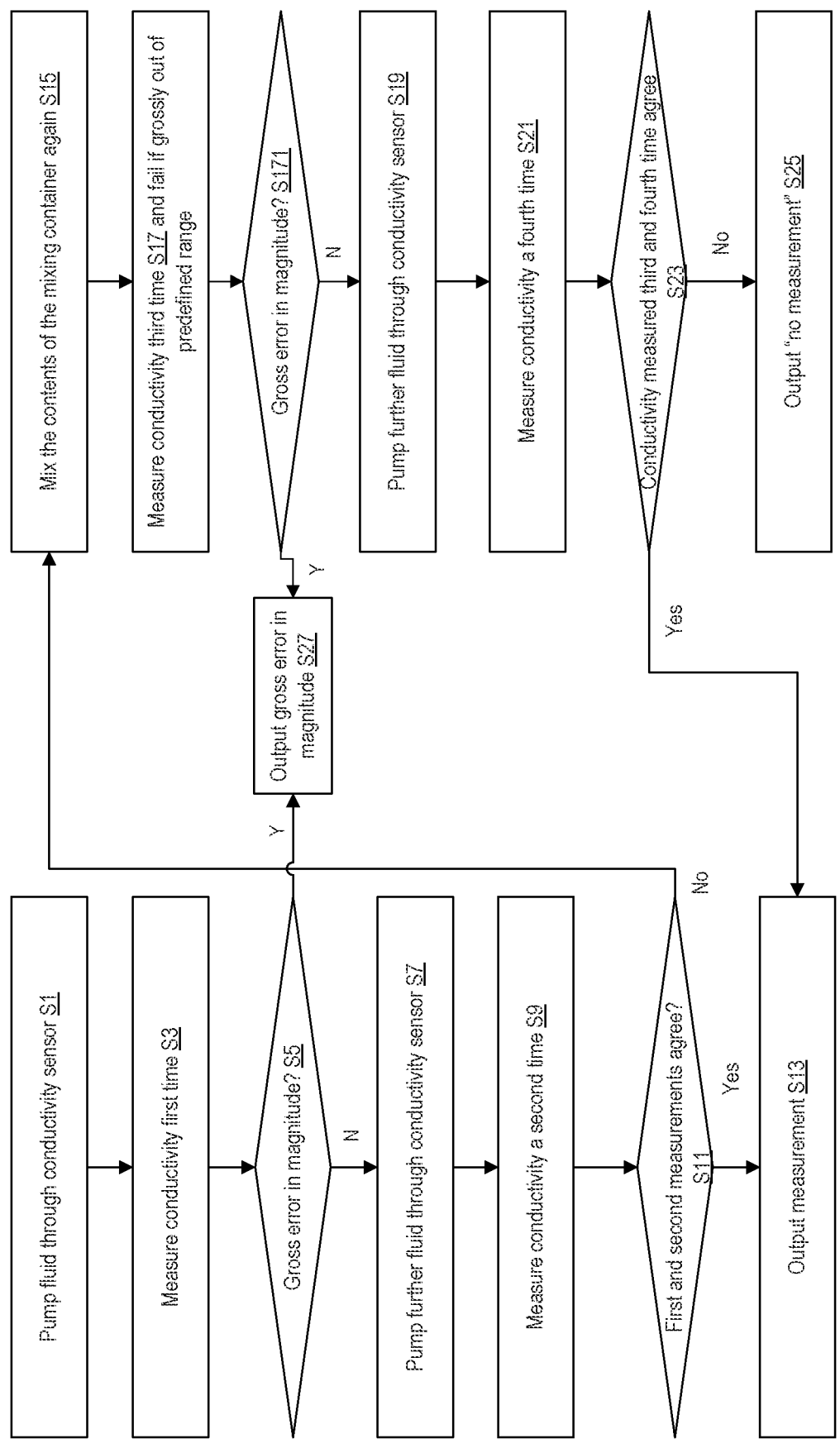
FIGS. 2A and 2B show a flow chart of a method for preparing a ready-to-use medicament according to embodiments of the disclosed subject matter.

FIG. 2A shows a procedure for reliably measuring the conductivity of a fluid. The fluid circuit will be configured as shown in FIG. 7. In this procedure two consecutive measurements are made of conductivity and temperature at different times so that the conductivity is measured for two different parts of a flow stream. The two consecutive measurements can be made with a single sensor 159 at two different times, or they may be made using two different sensors such as 159c and 159s. If the two different readings are within a predefined range of each other, the controller 141 mixes the mixing container 102 a second time. The measurements are compared again and if the two conductivity are within a predefined range of each other, the measurement is output as correct. If the two measurements show a difference in concentration beyond the predefined range, then the mixing container is mixed again (configuration of FIG. 6) and two consecutive measurements are taken again. The contents of drain line 147 may be purged to the drain. The rationale behind this is that a difference in magnitude of the consecutive measurements may be caused by inadequate mixing. If, after mixing again and repeating the two consecutive measurements, the magnitudes are still outside of the predefined range of each other, then the controller outputs a measurement failure or data indicating "no measurement." Also, after the initial measurement the controller determines if there is gross disparity between the measurement and a predefined or calculated estimate then the algorithm will immediately output an indication and stop the process.

Referring to FIG. 2A, at 51, the fluid whose conductivity is to be measured is pumped through conductivity/temperature sensors 159c and 159s by opening the conductivity sensor clamp 140 and closing the others, as shown in FIG. 7. At S3, the peristaltic pump 129 is run in a direction indicated by the arrows as shown in FIG. 7. The conductivity is measured a first time by flowing mixed fluid from the mixing container 102 through the temperature and conductivity sensors 159c and 159s (or single conductivity sensor 159, depending on the configuration of the system) and storing a magnitude or multiple magnitude readings thereof. If the absolute value of the difference between the measured conductivity readings is greater than a predefined magnitude at S5, then control goes to S27 where an error indication is output. Otherwise, at S7, additional fluid is pumped from the mixing container 102 and at S9, the conductivity is measured a second time at S9. At S11 it is determined if the first and second measurements agree within a predefined range. If the measurements differ by less a than predefined range, then the measurement is output at S13 where the output measurement may be one of the first and second measurements or an average of the measured values. If the measurements differ by more than the predefined range, then control proceeds to S15 where the mixing container contents are mixed again (because it is assumed that the measurements may differ due to insufficient mixing such that the medicament is not yet uniformly mixed in the mixing container 102). At S17, a third measurement for the conductivity is obtained. If the measured conductivity differs from the expected conductivity by a predefined magnitude at 5171, a gross error is detected at S27. Otherwise, the process continues at S19, where the mixing container contents are again pumped through the conductivity sensors 159c and 159s and a fourth measurement of conductivity is made at S21 in the manner described above. At S23 it is determined if the third and fourth measurement are within the predefined range and if so, at S25, the measured values (average of the two sensors or one of them) are output at S13 as a valid conductivity measurement. If the measured values still disagree by the predefined amount, then at S25 a failure is output.

Note that the consecutive measurements may be done sequentially in time using one temperature-compensated conductivity measurement indicated by conductivity/temperature sensor 159c, only. The fluid then is conveyed, and a temperature-compensated conductivity measurement is measured again by the same sensor. In alternative embodiments, separate pairs or single temperature-compensating may be separated along a line and the measurement generated by them may be compared instead.

Figure 2B:
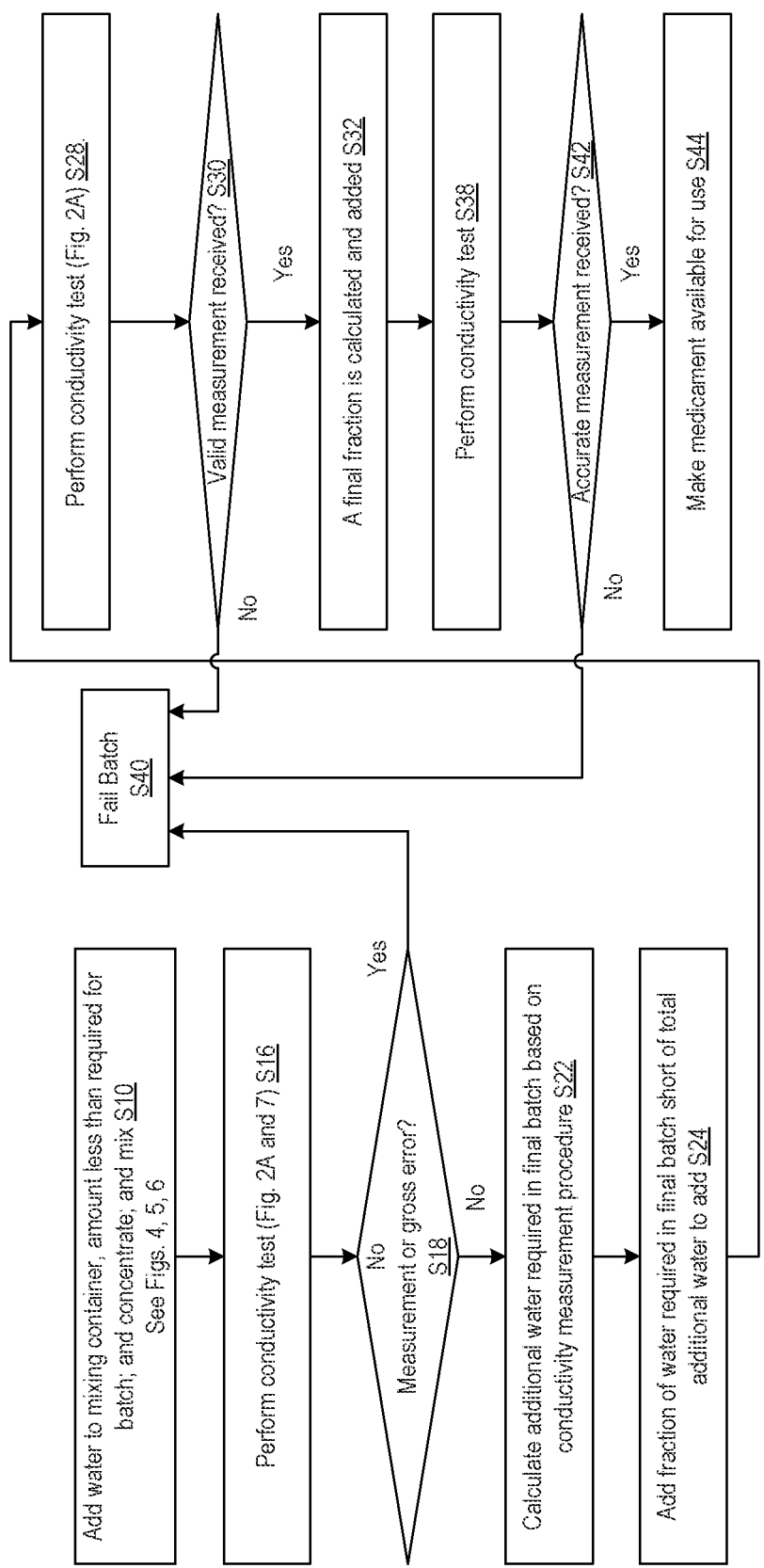

FIG. 2B shows a flow chart for a procedure that may be executed by the controller 141 with respect to the embodiment of FIG. 1A, 1B, or 1C. It incorporates the procedure of FIG. 2A by the reference to "conductivity test" described with reference to the procedure of FIG. 2A. When the conductivity test is referenced it means the procedure of FIG. 2A is entered and upon exiting proceeds to the next procedure element in FIG. 2B.

At S10, water is added by pumping it into the mixing container 102 from the purified water source 133. This is done by placing the system in the configuration of FIG. 4. The water pump 113 and the peristaltic pump 129 are activated for a predefined number of cycles or a predefined time interval, resulting in a quantify of water being conveyed along water line 142, through opened valve 138, through transfer line 149, through peristaltic pump 129 and through connector line 123 into mixing container 102.

Figure 4:
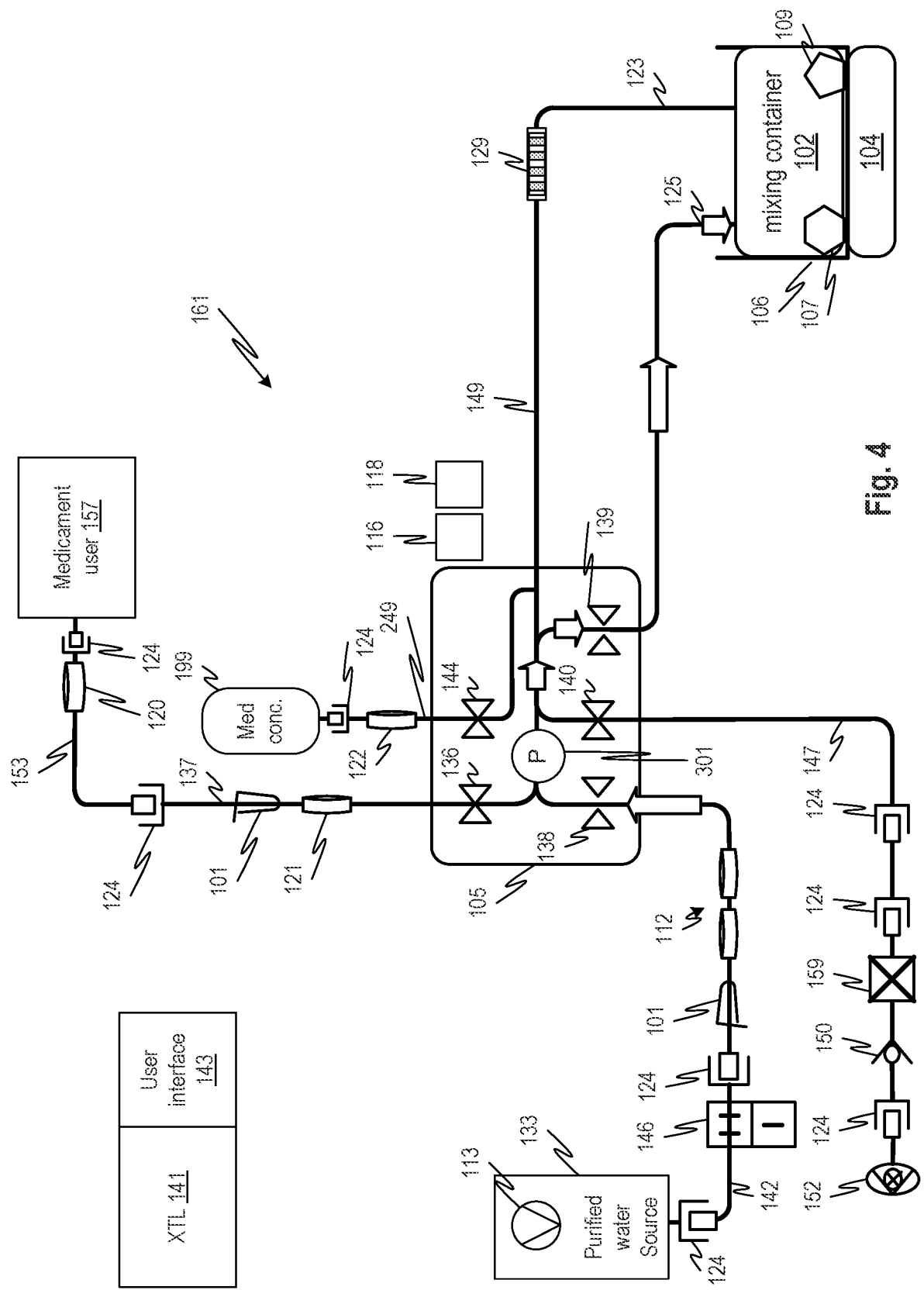
FIG. 4 shows configurations of the systems providing water to a mixing container according to embodiments of the disclosed subject matter.

As shown in FIG. 4, valve 139 can be opened so that the water pump 113 alone, without the involvement of peristaltic pump 129, conveys water into the mixing container 102 through line 125. Alternatively, valve 139 can be closed and peristaltic pump 129 operates to move water from water supply line 149 to inlet line 123 and through the inlet line 123 into mixing container 102.

It will be understood that the two pumps 113 and 129 are controlled such that the water pressure in the line is below the cracking pressure of the check valve 154 in the embodiment of FIG. 1B. This way, the water enters the mixing container only through supply line 123. On the other hand, in the embodiment of FIGS. 1A and 1C, the additional valve 139 can be closed to ensure that water does not flow through supply line 125. Note that valve 139 is not present in the embodiment of FIG. 1B. Further, the pumps are controlled to hold a steady pressure to provide a consistent upstream pressure for the peristaltic pump 129.

The amount of fluid conveyed at S10 may be a fraction of the total estimate required for a sufficient level of dilution, such as 50% of the expected total water volume.

Figure 5:
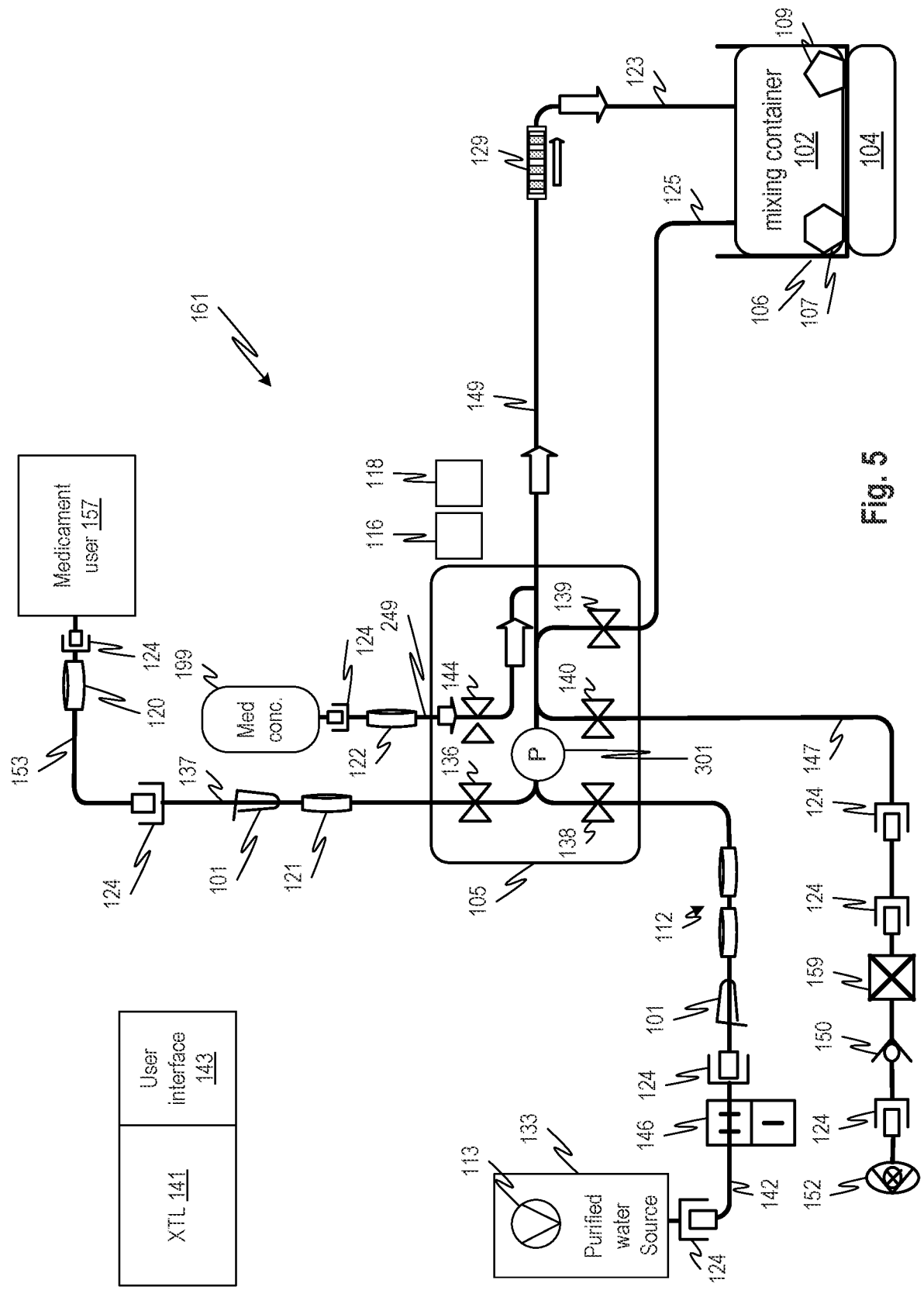
FIG. 5 shows configurations of the systems providing medicament concentrate to the mixing container according to embodiments of the disclosed subject matter.

Next, a quantity of concentrated medicament 199 is conveyed from the medicament container through medicament supply line 249, past the valve 144 into supply line 149 and through the supply line 129 into mixing container 102, as shown in the configuration of FIG. 5. It is noted that in this configuration, valve 144 is opened while valve 139 is closed. At this stage in the process a quantity of concentrated medicament and water is present in mixing container 102. As noted above, the quantity of water that is present may be smaller than the final quantity of water that is expected to be needed to completely dilute the concentrated medicament into its final concentration. Then, the contents of the mixing container 102 are mixed as shown in the configuration of the system in FIG. 6.

Next, at S16, the conductivity of the mixing container contents is measured by performing a conductivity test, described in FIG. 2A, as all of the medicament concentrate is already present in the mixing container 102, so the only possible action is the addition of water. To avoid over-dilution, water is added incrementally, and the conductivity is checked to reduce the possibility of over-dilution.

At S18, the controller determines whether the first measurement indicates a gross error by comparing the measured value of conductivity to a fixed predefined range of magnitude representing reasonable conductivities. If the measured value is outside the range, a gross error signal is output, and the batch is failed at S40. If not, the control proceeds to S22 where the additional water, based on the correctly measured value, is calculated. The calculation may be based on a dilution formula or a look-up table, among other options. A fraction of this calculated amount is added at S24. The addition of only a fraction at this stage provides a further margin of error, in case there is inaccuracy in the measurement of the water being added (e.g., due to inaccuracy of a peristaltic pump). Then at S28, the conductivity test is performed again. If the measurement is valid at S30, then a final fraction of water is calculated at S32 and added to the mixing container. The calculation of the final amount of water can take into account the expected conductivity at this stage and the measured conductivity, as a reflection of the accuracy of the metering of water, and this can be used to more finely calibrate the pump(s) that supply water, to provide a correct final concentration of medicament. A conductivity test is again performed at S38. If the measurement is deemed correct at S42, then the medicament is made available for use at S44. If not, then the batch is failed at S40. A failed batch may result in a message or alert output via the user interface 143. In embodiments, the failed batch may be drained from the system through drain line 147. In embodiments, one or more samples of the failed batch may be stored in testing containers in the system (not illustrated) for later analysis and troubleshooting of the system.

Note there may be a single conductivity/temperature sensor, or a pair of conductivity/temperature sensors as shown. A pair of conductivity/temperature sensors may provide a check against poor accuracy or failure of one of the sensors. The fluid from the mixing container flows through the drain conductivity line 147 using the peristaltic pump 129.

Figure 3:
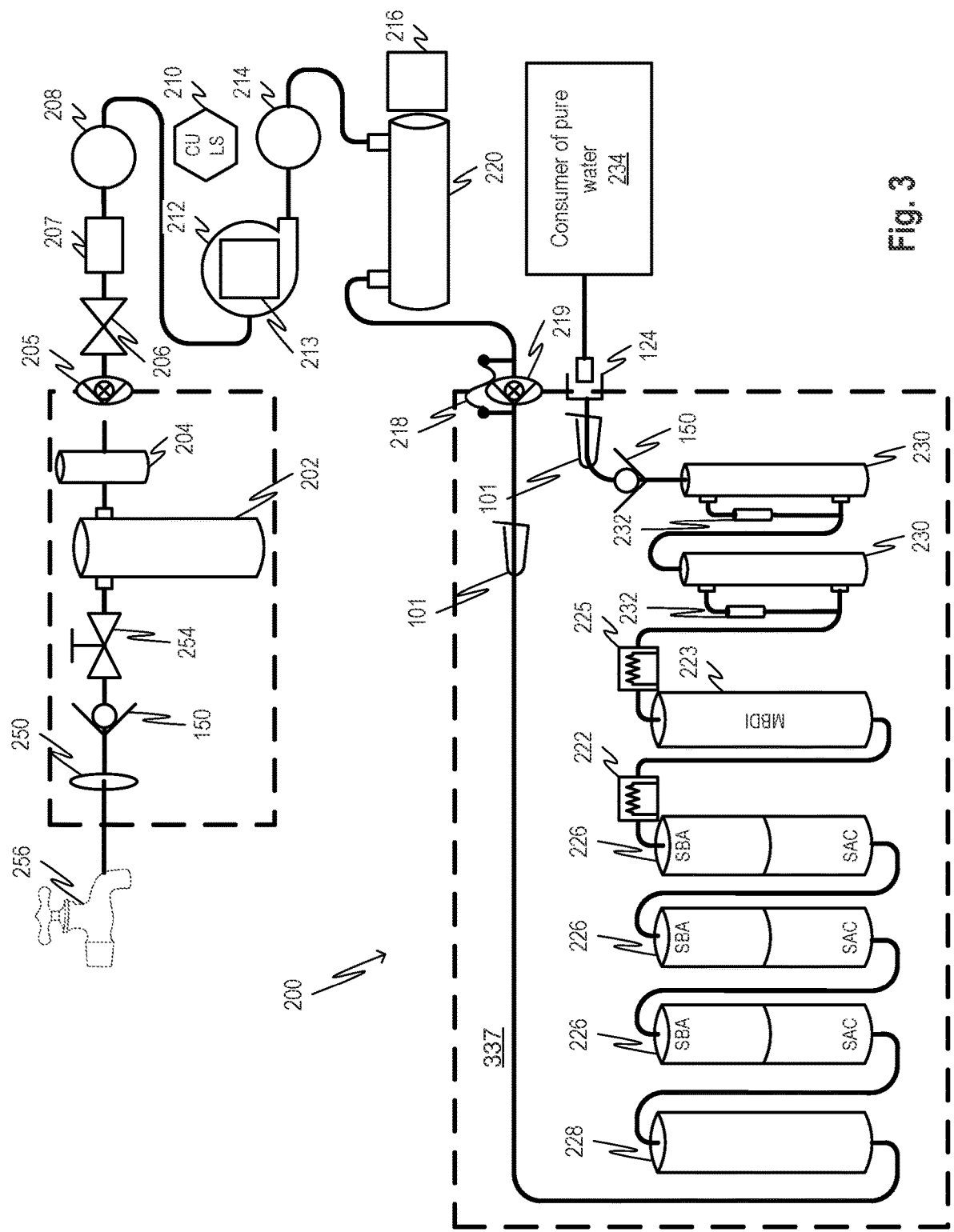
FIG. 3 shows a system for generating purified water for the system and method of FIGS. 1A and 1B according to embodiments of the disclosed subject matter.

FIG. 3 shows a water treatment plant 200 that may constitute an embodiment the purified water source 133. The water treatment plant 200 has an initial pretreatment stage that includes a connector 250 to connect to an unfiltered water source 256, for example a water tap. The water flows through a check valve 150, through a pressure regulator 254, and then through a sediment filter 202. The check valve 150 prevents backflow of the water. The water then flows through an air vent 204 that removes air from the water. The water then flows through a connector 205 that connects to a water shutoff clamp 206, a snubber 207, and a water inlet pressure sensor 208. Water is pumped by water pump 212 which has an encoder 213 for precise tracking of the water pump 212 speed. The snubber 207 reduces pressure fluctuations. The water then flows through a water output pressure sensor 214, through an ultraviolet light lamp 220 and into a filter plant 337 that performs deionization, carbon filtration, and sterilizing filtration. A UV light sensor 216 may be provided to detect whether the ultraviolet light lamp 220 is operating, so that it can be replaced if it becomes inoperable. A first-use-fuse 218 together with a connector 219 is provided on the inlet of sterilizing filter plant 337, such that the fuse indicates whether the filter plant 337 has been used. This helps reduce the likelihood that a previously-used filter plant is reused unintentionally. A combined control unit and leak sensor are indicated at 210. In the sterilizing filter plant 337, the water flows through a carbon filter 228 and three separated bed deionization filters 226 which may be resin separated bed filters. The water then flows through a mixed bed deionization filter 223 which follows the separated bed filters 226. The mixed bed deionization filter 223 may be a resin mixed bed filter. The water then flows through first and second ultrafilters 230, which follow the mixed bed deionization filter 223, and into the consumer of pure water 234. The embodiments of FIGS. 1A-1C are examples of a consumer of pure water 234.

Between a last separated bed deionization filter 226 and the mixed bed deionization filter 223 is a resistivity sensor 222 which indicates when the separated bed deionization filters 226 are nearing exhaustion, or at exhaustion. The mixed bed deionization filter 223 is still able to hold a predefined minimum magnitude of resistivity but the separated bed deionization filters 226 and the mixed bed deionization filter 223 may be replaced at the same time. In embodiments, along with the separated bed deionization filters 226 and the mixed bed deionization filter 223, the carbon filter 228 and ultrafilters 230 along with the interconnecting lines and other components may also be replaced as a single package. A current treatment can be completed in reliance on the mixed bed deionization filter 223 before the exhausted filters are replaced. A further resistivity sensor 225 detects unexpected problems with the mixed bed deionization filter 223 upstream from the separated bed deionization filters 226, which may require shutdown of the treatment and immediate replacement of the filters. Note that each of the ultrafilters 230 has an air vent 232. A check valve 150 is located downstream of the ultrafilters 230. The consumer of pure water 234 may be unit such as that of FIGS. 1A-1C which mixes a batch of medicament for use by a medicament user 157 such as a peritoneal dialysis cycler or any other type of medicament consuming device.

It should be evident from the above that the procedures of FIG. 2B in combination with those of FIG. 2A may be performed using the embodiments of FIGS. 1A-1C.

Note in any of the embodiments where the term clamp is used, it should be recognized that the functional element includes a tube or other flexible conduit and the clamp so that it functions as a valve. In any of the embodiments, another type of valve may be substituted for the clamp and conduit to provide the same function. Such a variation may be considered to alternative embodiments and clamp and conduit are not limiting of the subject matter conveyed herein.

Note that in any of the embodiments that identify a bag as the container, any bag may be replaced by any container including those of glass, polymer and other materials. In any embodiment where flow control is performed by a clamp, it should be understood that in any embodiment, including the claims, any clamp can be replaced by another type of valve such as a stopcock valve, a volcano valve, a ball valve, a gate valve or other type of flow controller. It should be understood that a clamp in the context of the disclosed subject matter is a clamp that closes around a tube to selectively control flow through the position of the clamp. Note that in any of the embodiments, the order of adding and mixing to the mixing container 102 can by reversed from what is described with respect to the embodiments. In any of the embodiments instead of dextrose concentrate being used, this can be substituted for glucose or another osmotic agent.

FIG. 4 shows a first step that adds water to the mixing container 102 from the water source 133. The peristaltic pump 129 runs in a direction to pump water through the first mixing container connector line 123 and all clamps are closed except for clamp 138. Optionally, clamp 139 may be opened, as shown.

Referring to FIG. 4, water is provided from the purified water source 133 to the system. The peristaltic pump 129 is configured to move fluid in a line 123 connected to the mixing container 102. The peristaltic pump 129 also moves fluid, at selected times, through the line 125 which returns the fluid to the mixing bag. Line 125 can be provided with a check valve 154 (FIG. 1B) which prevents flow in one direction and has a cracking pressure which must be overcome for water to flow in the other direction. In the example of FIG. 1B, the check valve permits water to flow through line 125 toward the mixing container 102 when the cracking pressure of the check valve 154 is overcome. Initially, the purified water from the purified water source 133 is pumped by the water pump 113 with water inlet clamp 138 open and the batch release clamp 136 and the conductivity sensor clamp 140 closed such that water is pumped into the mixing container 102 through line 123 with the peristaltic pump 129 running so as to convey water into the mixing container 102, as shown in FIG. 4.

Still Referring to FIG. 4, the peristaltic pump 129 may remain turned off while clamp 139 is opened, thereby allowing pressure generated by pump 113 to convey the purified water through line 125 into mixing container 102.

FIG. 5 illustrates the configuration of the system when medicament concentrate 199 flows into the mixing container 102. As shown in the figure, valve 144 is opened and peristaltic pump 129 can operate in reverse direction relative to when it is used to fill the mixing container 102 with water, such that the concentrate flows through inlet line 123 into mixing container 102. In an alternate embodiment, the medicament concentrate 199 can be positioned sufficiently high or above mixing container 102 that a gravity powered fill can be accomplished. In this scenario, valve 144 is opened and valve 139 is opened which permits gravity to convey the medicament concentrate through inlet line 125 into mixing container 102.

Figure 6:
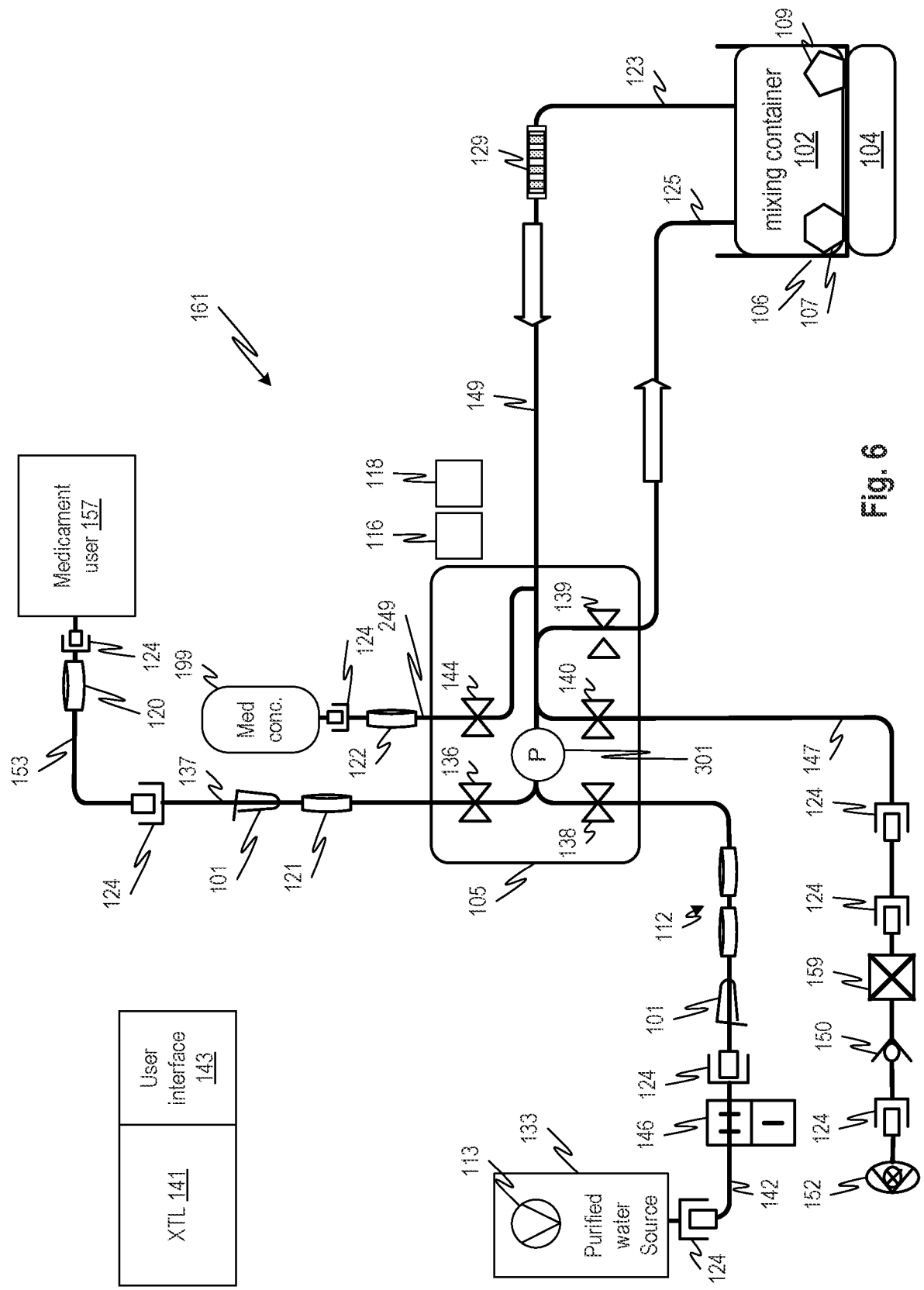
FIG. 6 shows configurations of the systems mixing the content of the mixing container according to embodiments of the disclosed subject matter.
Figure 7:
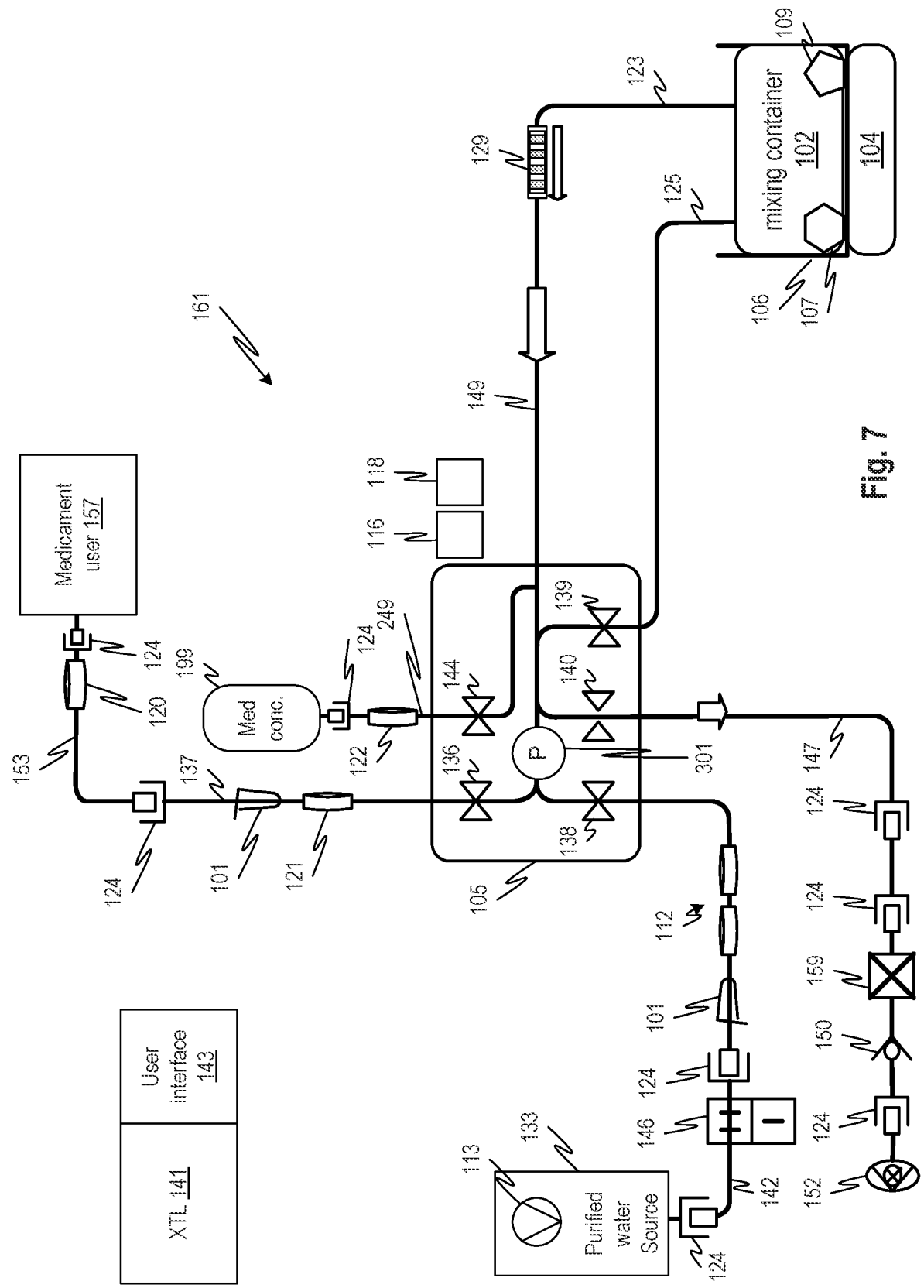
FIG. 7 shows various configurations of the systems testing conductivity of the content of the mixing container according to embodiments of the disclosed subject matter.

Referring to FIG. 6, to mix the contents of the mixing container 102 the peristaltic pump 129 pumps fluid in a circular path through lines 123 and 125 with all the clamps closed except for clamp 139. Then the contents of the mixing container 102 are mixed by the flow circulating through the mixing container 102. It will be noted that because there is no check valve on line 125 in this embodiment, the peristaltic pump 129 does not have to generate pressure which is sufficient to overcome the cracking pressure of the check valve 154 that is shown in FIG. 1B.

Referring to FIG. 7, after a sufficient time of mixing, a sample of the fluid in the mixing container 102 may be pumped through a drain conductivity line 147 which contains conductivity/temperature sensors 159c and 159s (control sensor 159c and safety sensor 159s) to determine a temperature-compensated conductivity of the diluted medicament. Each sensor 159c and 159s may be configured to calculate conductivity and temperature of fluid passing through or past the sensor. Valve 140 is opened and the peristaltic pump 129 operates in reverse direction as shown in the figure. Two redundant sensors 159c and 159s may be provided, to enable a comparison of their respective measurements and thereby to confirm that the sensors are functioning. If their respective measurements are within a predetermined range, the sensors are understood to be functioning correctly. On the other hand, if their respective measurements are outside of the predetermined range, an error condition may be signaled as described below.

Figure 8:
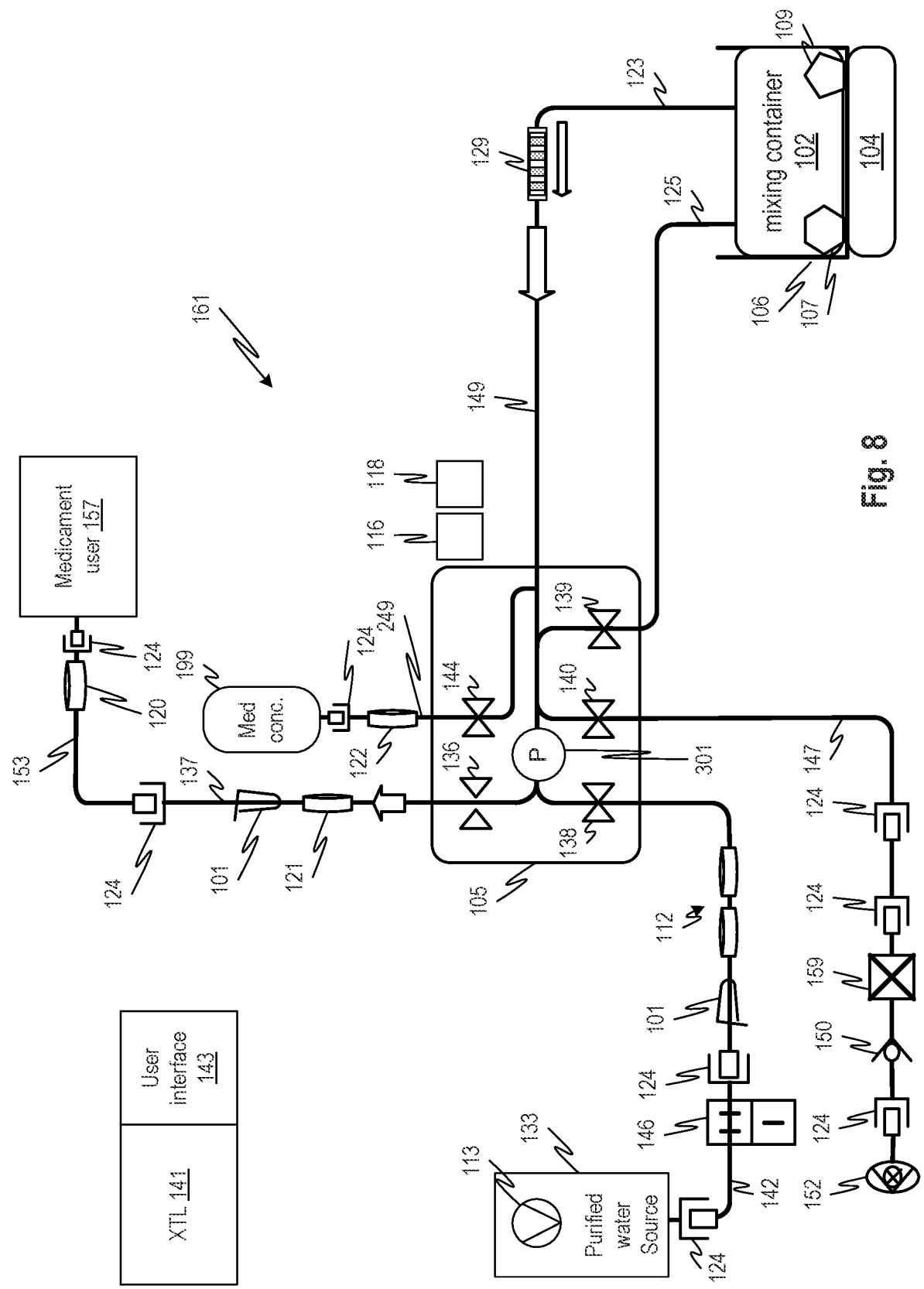
FIG. 8 shows configurations of the systems providing the content of the mixing container to a consumer of the content according to embodiments of the disclosed subject matter.

Referring now to FIG. 8, once of the medicament is prepared and mixed in the mixing container at 102, and the medicament is deemed to be ready for use, the batch release clamp 136 is open and the water inlet clamp 138 and the conductivity sensor clamp 140 are closed. A pump 115 in a medicament user 157 may then draw fluid from the circular path as the peristaltic pump 129 rotates to maintain fluid at the cracking pressure of the check valve 154 in FIG. 1B, or at a pressure that is controlled based on a pressure signal from pressure sensor 301, if no cracking check valve is used (e.g., FIG. 1A, 1C). At this time, the water inlet clamp 138 and the conductivity sensor clamp 140 are closed. The medicament user 157 may be any type of treatment device or container that receives the mixed medicament from the mixing container 102. In embodiments, the cracking pressure may be 3.5 PSI. It will be understood that this makes the medicament preparation system appear like a bag of dialysate with a head pressure of 3.5 PSI.

A medicament pump 115 in the medicament user 157 may see a positive pressure at the cracking pressure type check valve 154 cracking pressure, which may facilitate the pump 115 of the medicament user 157 by mimicking the pressure of an elevated medicament container with a head pressure approximately at the cracking pressure of the check valve 154. In embodiments, clamp 139 is closed while peristaltic pump 129 operates in the direction shown in the drawing. Clamp 136 is opened and the medicament is conveyed through supply lines 137 and 153 to medicament user 157. A pressure sensor 301 is provided to measure the pressure in this fluid channel and to provide a signal, which may be used in feedback control, to modulate the speed of the peristaltic pump 129 and thereby provide a predetermined pressure in the formed fluid channel. In further embodiments, the peristaltic pump 129 is not used, and instead medicament user pump 115 operates to draw the medicament from the mixing container 102. Clamp 139 and clamp 136 are both opened, thereby providing a fluid path between the mixing container 102 and the medicament user 157. It is possible to elevate mixing container 102 to such a level that it provides a positive pressure (head pressure) for the medicament user 157.

Note that temperature-compensated conductivity is intended to refer to a number that is proportional to concentration and may be determined in various ways including but not limited to a lookup table and a formula. For the remainder of this disclosure, a reference conductivity may be understood to mean temperature-compensated conductivity or an actual calculation of concentration. That is, the temperature-compensated conductivity may be a value that is generated by the controller by multiplying the measured conductivity with a value that represents the rate of change of concentration with temperature. In other embodiments, the controller 141 may calculate a concentration directly using a look-up table or formula.

As noted above, the mixing container at 102 may be part of a disposable unit 161. Included in a disposable unit 161 are a source medicament supply line 137, transfer line 149, water source line 142, drain conductivity line 147 and the mixing container 102. The disposable unit 161 is permanently interconnected up to and including an end of each of the connectors 124. Also included in the disposable unit 161 may be the check valve 154 that has a predefined cracking pressure (e.g., 3.5 PSI). The disposable unit 161 can be connected to check valve 150 which prevents back flow in the drain conductivity line 147. Mixed fluid is pumped through temperature and conductivity sensors 159c and 159s and is determined to be mixed when two consecutive measurements of the conductivity of mixed fluid flowing through the temperature and conductivity sensors 159c and 159s are within a predefined range of each other. If two consecutive measurements of the conductivity differ by a margin greater than the predefined range, the mixing container 102 may be mixed again. An attachment to drain or waste container is provided by a connector 152. Note the mixing bag may contain a liquid or dry concentrate which forms part of the disposable unit 161.

A door lock 116 is provided adjacent a user interface door 105 to lock the user interface door. A physical door 105 that opens encloses and provides access to the interior of the fluid preparation system may have a user interface on it which may be a part of user interface 143. A door sensor 118 detects whether the door lock is in an open or a locked position to ensure that all clamps and the peristaltic pump actuators are fully engaged with the disposable fluid circuit.

The door sensor 118 may include a plunger which is pressed in when the door is closed and outputs an electrical signal to indicate whether or not the door is closed. In other embodiments, the door sensor 118 may include a magnetic reed switch which detects the presence or the absence of a magnet which is located on the door 105 at a location which is detectable by the reed switch. Purified water flows into the disposable circuit where a pair of 0.2 micron filters (also in the disposable unit 161) are located to ensure that any touch contamination is prevented from flowing into the disposable circuit. An optional sterilizing filter 120 may be provided in a user medicament supply line 153. The mixing container 102 of the disposable unit 161 may have sufficient volume for a single treatment or in embodiments, multiple treatments. To make a batch of dilute concentrate, water is pumped into the mixing container 102 which contains concentrate sealed in it as-delivered.

The medicament output line 137 may include an optional air removal filter 121. The air removal filter 121 may be a 1.2 µm filter which removes air.

The check valve 150 in drain conductivity line 147 ensures the flow does not reverse to safeguard against contamination in the medicament or water lines or other sterile fluid circuits. Note that the peristaltic pump 129 is regulated to ensure the output pressure remains below the cracking pressure of the check valve 154 when the conductivity of the mixing container contents is measured.

Figure 9:
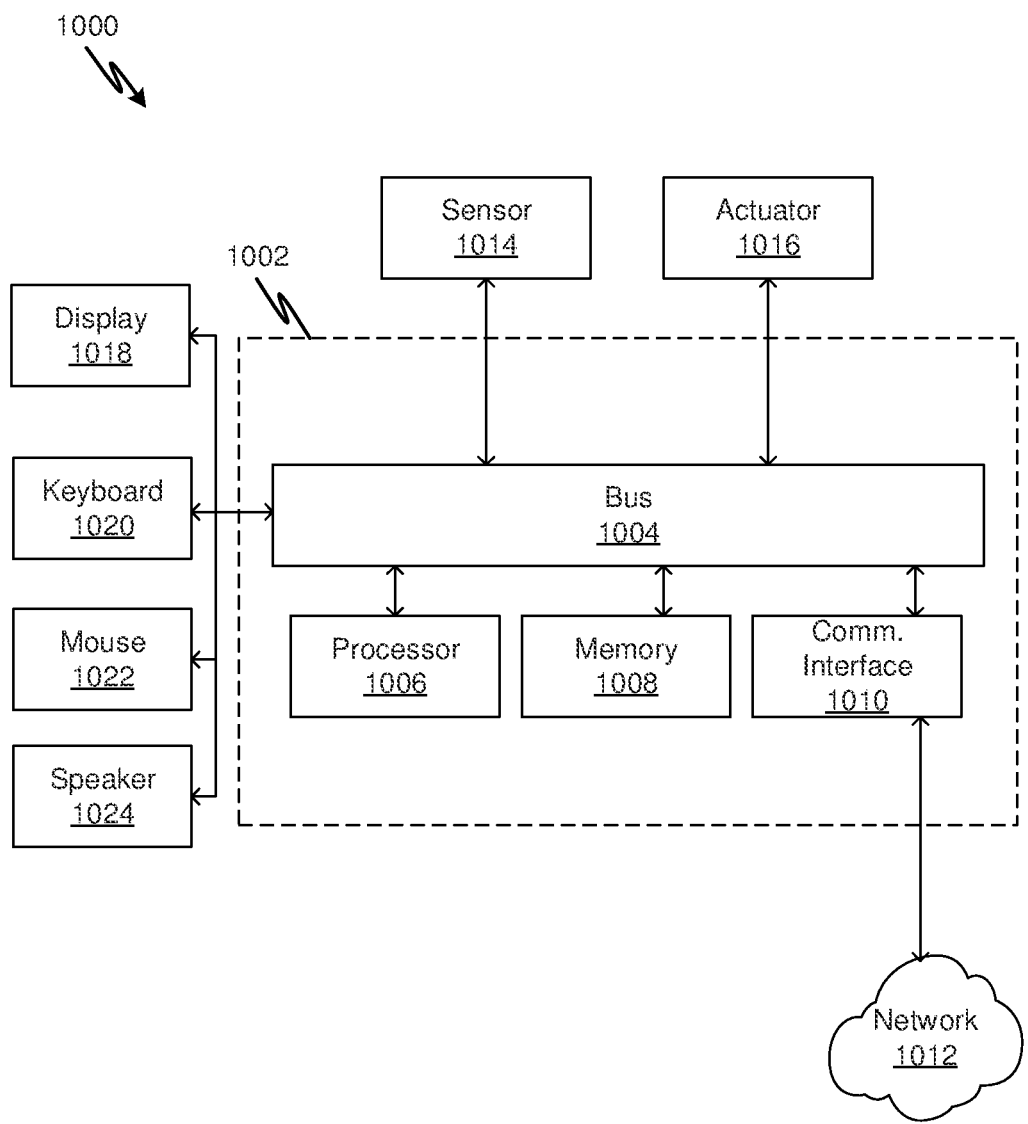
FIG. 9 shows a computer system that may describe the functions and elements of a controller as described herein and in accordance with the embodiments of the disclosed subject matter.

FIG. 9 shows a block diagram of an example computer system according to embodiments of the disclosed subject matter. In various embodiments, all, or parts of system 1000 may be included in a medical treatment device/system such as a renal replacement therapy system. In these embodiments, all, or parts of system 1000 may provide the functionality of a controller of the medical treatment device/systems. In some embodiments, all, or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/ objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with one or more sensors 1014 and one or more actuators 1016, each providing respective functionality in accordance with various embodiments disclosed herein, for example, for measuring signals.

It will be appreciated that the modules, processes, systems, and sections described above can be implemented in hardware, hardware programmed by software, software instruction stored on a non-transitory computer readable medium or a combination of the above. For example, a method for providing a medicament to a medicament user can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems of medical devices and/or computer programming arts.

Moreover, embodiments of the disclosed method, system, and computer program product can be implemented in software executed on a programmed general-purpose computer, a special purpose computer, a microprocessor, or the like.

According to a first further embodiment, there is provided a system for preparing a medicament for use by a medicament user, including: a proportioning machine with a controller (141, 1002) and pumping and clamping actuators (1016) to engage a fluid circuit having pumping and clamping portions that engage with respective actuators among the pumping and clamping actuators (1016); the fluid circuit having an empty mixing container (102) attached to the fluid circuit; a detachable container (199) having concentrated medicament therein; the proportioning machine being configured to flow fluid from the mixing container (102) into and out of the mixing container (102) to circulate the fluid; the proportioning machine being configured to flow water and the concentrated medicament into said mixing container (102) to dilute the concentrated medicament to make a ready-to-use medicament; the proportioning machine controller (141) being configured to regulate a clamp (139) on a return line (125) leading to said mixing container (102) to generate a predefined pressure in an outlet line (137, 153) of the fluid circuit which is attachable to an external user (157) of the ready-to-use medicament; and the predefined pressure being maintained in the outlet line (137, 153) by pressure feedback control.

According to a second further embodiment, there is provided the system of the first further embodiment, wherein the clamp (139) is a controllable clamp that regulates flow and pressure in a line (125). According to a third further embodiment, there is provided the system of the first further embodiment or any of the other foregoing embodiments, wherein the concentrate and ready-to-use medicament are for peritoneal dialysis fluid. According to a fourth further embodiment, there is provided the system of the first further embodiment or any of the other foregoing embodiments, wherein the external user (157) of the ready-to-use medicament is a peritoneal dialysis cycler. According to a fifth further embodiment, there is provided the system of the first further embodiment or any of the other foregoing embodiments, wherein the medicament is removably connected to the fluid circuit by connectors (124). According to a sixth further embodiment, there is provided the system of the first further embodiment or any of the other foregoing embodiments, wherein the pumping and clamping actuators (1016) include a peristaltic pump actuator. According to a seventh further embodiment, there is provided the system of the first further embodiment or any of the other foregoing embodiments, wherein the fluid circuit is connectable to a source of purified water (133). According to an eighth further embodiment, there is provided the system of the first further embodiment or any of the other foregoing embodiments, wherein the fluid circuit is a single-use consumable.

According to a ninth further embodiment, there is provided a system for preparing a medicament for use by a medicament user (157), including: a proportioning machine with a controller (141, 1002) and pumping and clamping actuators (1016) to engage a fluid circuit having pumping and clamping portions that engage with respective actuators among the pumping and clamping actuators (1016); the fluid circuit having a sterilized mixing container (102) connected to the fluid circuit; a concentrate container (199) having concentrated medicament therein; the proportioning machine being configured to flow fluid from the mixing container (102) into and out of the mixing container (102) to circulate the fluid; the proportioning machine being configured to flow water into said mixing container (102) to dilute the concentrated medicament to make a ready-to-use medicament; and the concentrate container (199) being removably connected to the fluid circuit by connectors (124).

According to a tenth further embodiment, there is provided the system of the ninth further embodiment or any of the other foregoing embodiments, wherein the concentrate and ready-to-use medicament are for peritoneal dialysis fluid. According to an eleventh further embodiment, there is provided the system of the ninth further embodiment or any of the other foregoing embodiments, wherein the medicament user (157) of the ready-to-use medicament is a peritoneal dialysis cycler. According to a twelfth further embodiment, there is provided the system of the ninth further embodiment or any of the other foregoing embodiments, wherein the proportioning machine controller (141, 1002) is configured to regulate a clamp (139) on a return line (129) leading to said mixing container (102) to generate a predefined pressure in an outlet line (137, 153) of the fluid circuit which is attachable to an external user (157) of the ready-to-use medicament, wherein the predefined pressure is maintained in the outlet line (137, 153) by pressure feedback control. According to a thirteenth further embodiment, there is provided the system of the twelfth further embodiment or any of the other foregoing embodiments, wherein the clamp (139) is a controllable clamp that regulates flow and pressure in a line (125). According to a fourteenth further embodiment, there is provided the system of the ninth further embodiment or any of the other foregoing embodiments, wherein the pumping and clamping actuators (1016) include a peristaltic pump actuator. According to a fifteenth further embodiment, there is provided the system of the ninth further embodiment or any of the other foregoing embodiments, wherein the fluid circuit is connectable to a source of purified water (133). According to a sixteenth further embodiment, there is provided the system of the ninth further embodiment or any of the other foregoing embodiments, wherein the fluid circuit is a single-use consumable.

According to a seventeenth further embodiment, there is provided a method for preparing a ready-to-use medicament for use by a medicament user (157), including: pumping a first quantity of water into a mixing container (102) in a fluid circuit of a medicament preparation system, the first quantity of water being less than a total quantity of water required in a final batch of medicament; flowing concentrated medicament from a medicament container (199) to the mixing container (102) to form a fluid with the first quantity of water, and pumping the fluid in a circular path through the mixing container (102) to form a first mixed fluid; performing a first conductivity measurement on the first mixed fluid; in response to a controller (141, 1002) of the medicament preparation system determining there is no error in a result of the first conductivity measurement, adding a second quantity of water to the first mixed fluid and pumping the first mixed fluid with the second quantity of water in the circular path through the mixing container (102) to form a second mixed fluid, the second quantity of water being less than a remaining quantity of water required in the final batch of medicament; performing a second conductivity measurement on the second mixed fluid; and in response to the controller (141, 1002) determining there is no error in a result of the second conductivity measurement, adding a third quantity of water to the second mixed fluid and pumping the second mixed fluid with the third quantity of water in the circular path through the mixing container (102) to form the final batch of medicament; performing a third conductivity measurement on the final batch of medicament; and in response to the controller (141, 1002) determining there is no error in a result of the third conductivity measurement, pumping the final batch of medicament to the medicament user (157).

According to an eighteenth further embodiment, there is provided the method of the seventeenth further embodiment or any of the other foregoing embodiments, wherein the mixing container (102) is detachably connected to mixing container lines (123, 125) of the fluid circuit by connectors (124). According to a nineteenth further embodiment, there is provided the method of the seventeenth further embodiment or any of the other foregoing embodiments, wherein the medicament container (199) is detachably connected to the fluid circuit by a connector (124). According to a twentieth further embodiment, there is provided the method of the seventeenth further embodiment or any of the other foregoing embodiments, wherein the fluid circuit includes a first mixing line (123) connected to the mixing container (102), a second mixing line (125) connected to the mixing container (102) and the first mixing line (123), a water line (142) connecting a water (133) source to the first and second mixing lines (123, 125), a drain conductivity line (147) connected to the first and second mixing lines (123, 125), a medicament user supply line (137, 153) connecting the medicament user (157) to the first and second mixing lines (123, 125), and a concentrated medicament supply line (249) connecting the medicament container to the first mixing line (123), and wherein the pumping of the first quantity of water into the mixing container (102) includes pumping the first quantity of water into the mixing container (102) through the water line (142) and the first mixing line (123) at a pressure below a cracking pressure of a first check valve (154) on the second mixing line (125) while a water line valve (138) on the water line (142) is open, and a drain conductivity line valve (140) on the drain conductivity line (147), a batch release valve (136) on the medicament user supply line (137, 153), and a concentrated medicament supply valve (144) on the concentrated medicament supply line (249) are closed.

According to a twenty-first further embodiment, there is provided the method of the twentieth further embodiment or any of the other foregoing embodiments, wherein the pumping of the fluid in the circular path through the mixing container (102) includes pumping the fluid in the circular path sequentially through the first mixing line (123), the second mixing line (125), and the mixing container (102) while the water line valve (138), the drain conductivity line valve (140), the batch release valve (136), and the concentrated medicament supply valve (144) are closed.

According to a twenty-second further embodiment, there is provided the method of the twentieth further embodiment or any of the other foregoing embodiments, wherein the performing of the first conductivity measurement includes pumping a portion of the first mixed fluid through a conductivity sensor (159c, 159s, 1014) in the drain conductivity line (147) while the drain conductivity line valve (140) is open, and the water line valve (138), the batch release valve (136), and the concentrated medicament supply valve (144) are closed.

According to a twenty-third further embodiment, there is provided the method of the twentieth further embodiment or any of the other foregoing embodiments, wherein the pumping of the final batch of medicament to the medicament user (157) includes pumping the final batch of medicament through the medicament user supply line (137, 153) at a cracking pressure of the first check valve (154) while the batch release valve (136) is open, and the water line valve (138), the drain conductivity line valve (140), and the concentrated medicament supply valve (144) are closed, and wherein a second check valve (151) on the medicament user supply line (137, 153) has a cracking pressure that is lower than the cracking pressure of the first check valve (154).

According to a twenty-fourth further embodiment, there is provided the method of the seventeenth further embodiment or any of the other foregoing embodiments, wherein the fluid circuit includes a first mixing line (123) connected to the mixing container (102), a second mixing line (125) connected to the mixing container (102) and the first mixing line (123), a water line (142) connecting a water source (133) to the first and second mixing lines (123, 125), a drain conductivity line (147) connected to the first and second mixing lines (123, 125), and a medicament user supply line (137, 153) connecting the medicament user (157) to the first and second mixing lines (123, 125), and a concentrated medicament supply line (249) connecting the medicament container to the first mixing line (123), and wherein the pumping of the first quantity of water into the mixing container (102) includes pumping the first quantity of water into the mixing container (102) through the water line (142) and the first mixing line (123) while a water line valve (138) on the water line (142) is open, and a drain conductivity line valve (140) on the drain conductivity line (147), a batch release valve (136) on the medicament user supply line (137, 153), and a concentrated medicament supply valve (144) on the concentrated medicament supply line (249) are closed.

According to a twenty-fifth further embodiment, there is provided the method of the twenty-fourth further embodiment or any of the other foregoing embodiments, wherein a mixing valve (139) leading to the second mixing line (125) is closed during the pumping of the first quantity of water into the mixing container (102). According to a twenty-sixth further embodiment, there is provided the method of the twenty-fourth further embodiment or any of the other foregoing embodiments, wherein a mixing valve (139) leading to the second mixing line (125) is open during the pumping of the first quantity of water into the mixing container (102). According to a twenty-seventh further embodiment, there is provided the method of the twenty-fourth further embodiment or any of the other foregoing embodiments, wherein the performing of the first conductivity measurement includes pumping a portion of the first mixed fluid through a conductivity sensor (159c, 159s, 1014) in the drain conductivity line (137) while the drain conductivity line valve (140) is open, and the water line valve (138), a mixing valve (139) leading to the second mixing line (125), the batch release valve (136), and the concentrated medicament supply valve (144) are closed.

According to a twenty-eighth further embodiment, there is provided the method of the twenty-fourth further embodiment or any of the other foregoing embodiments, wherein the pumping of the final batch of medicament to the medicament user (157) includes pumping the final batch of medicament through the medicament user supply line (137, 153) while the batch release valve (136) is open, and the water line valve (138), a mixing valve (139) leading to the second mixing line (125), the drain conductivity line valve (140), and the concentrated medicament supply valve (144) are closed.

According to a twenty-ninth further embodiment, there is provided the method of the twenty-fourth further embodiment or any of the other foregoing embodiments, wherein the pumping of the final batch of medicament to the medicament user (157) includes pumping the final batch of medicament through the medicament user supply line (137, 153) while the batch release valve (136) and a mixing valve (139) leading to the second mixing line (125) are open, and the water line valve (138), the drain conductivity line valve (140), and the concentrated medicament supply valve (144) are closed.

According to a thirtieth further embodiment, there is provided the method of the seventeenth further embodiment or any of the other foregoing embodiments, wherein the performing of the first conductivity measurement includes: pumping a first quantity of the first mixed fluid through a conductivity sensor (159c, 159s, 1014) and measuring, by the conductivity sensor (159c, 159s, 1014), a conductivity of the first quantity of the first mixed fluid; in response to the controller (141, 1002) determining that a magnitude of the measured conductivity of the first quantity of the first mixed fluid is not greater than a predefined magnitude, pumping a second quantity of the first mixed fluid through the conductivity sensor (159c, 159s, 1014) and measuring, by the conductivity sensor (159c, 159s, 1014), a conductivity of the second quantity of the first mixed fluid; and in response to the controller (141, 1002) determining that the measured conductivity of the second quantity of the first mixed fluid differs from the measured conductivity of the first quantity of the first mixed fluid by less than a predefined range, outputting, by the controller (141, 1002), a measurement based on either one or both of the measured conductivity of the first quantity of the first mixed fluid and the measured conductivity of the second quantity of the first mixed fluid.

According to a thirty-first further embodiment, there is provided the method of the seventeenth further embodiment or any of the other foregoing embodiments, wherein the performing of the first conductivity measurement includes: pumping a first quantity of the first mixed fluid through a conductivity sensor (159c, 159s, 1014) and measuring, by the conductivity sensor (159c, 159s, 1014), a conductivity of the first quantity of the first mixed fluid; in response to the controller (141, 1002) determining that a magnitude of the measured conductivity of the first quantity of the mixed fluid is not greater than a first predefined magnitude, pumping a second quantity of the first mixed fluid through the conductivity sensor (159c, 159s, 1014) and measuring, by the conductivity sensor (159c, 159s, 1014), a conductivity of the second quantity of the first mixed fluid; in response to the controller (141, 1002) determining that the measured conductivity of the second quantity of the first mixed fluid differs from the measured conductivity of the first quantity of the first mixed fluid by more than a predefined range, further mixing the first mixed fluid through the mixing container (102) and subsequently pumping a third quantity of the first mixed fluid through the conductivity sensor (159c, 159s, 1014) and measuring, by the conductivity sensor (159c, 159s, 1014), a conductivity of the third quantity of the first mixed fluid; in response the controller (141, 1002) determining that a magnitude of the measured conductivity of the third quantity of the further mixed fluid is not greater than a second predefined magnitude, pumping a fourth quantity of the first mixed fluid through the conductivity sensor (159c, 159s, 1014) and measuring, by the conductivity sensor (159c, 159s, 1014), a conductivity of the fourth quantity of the first mixed fluid; and in response to the controller (141, 1002) determining that the measured conductivity of the fourth quantity of the first mixed fluid differs from the measured conductivity of the third quantity of the first mixed fluid by less than a predefined range, outputting, by the controller (141, 1002), a measurement based on either one or both of the measured conductivity of the third quantity of the first mixed fluid and the measured conductivity of the fourth quantity of the first mixed fluid.

It is, thus, apparent that there is provided, in accordance with the present disclosure, Medicament Preparation Devices, Methods, and Systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A method for preparing a ready-to-use medicament for use by a medicament user, comprising:

pumping a first quantity of water into a mixing container in a fluid circuit of a medicament preparation system, the first quantity of water being less than a total quantity of water required in a final batch of medicament;

flowing concentrated medicament from a medicament container to the mixing container to form a fluid with the first quantity of water, and pumping the fluid in a circular path through the mixing container to form a first mixed fluid;

performing a first conductivity measurement on the first mixed fluid;

in response to a controller of the medicament preparation system determining there is no error in a result of the first conductivity measurement, adding a second quantity of water to the first mixed fluid and pumping the first mixed fluid with the second quantity of water in the circular path through the mixing container to form a second mixed fluid, the second quantity of water being less than a remaining quantity of water required in the final batch of medicament;

performing a second conductivity measurement on the second mixed fluid; and in response to the controller determining there is no error in a result of the second conductivity measurement, adding a third quantity of water to the second mixed fluid and pumping the second mixed fluid with the third quantity of water in the circular path through the mixing container to form the final batch of medicament;

performing a third conductivity measurement on the final batch of medicament; and in response to the controller determining there is no error in a result of the third conductivity measurement, pumping the final batch of medicament to the medicament user.

2. The method of claim 1, wherein the mixing container is detachably connected to mixing container lines of the fluid circuit by connectors.

3. The method of claim 1, wherein the medicament container is detachably connected to the fluid circuit by a connector.

4. The method of claim 1, wherein the fluid circuit includes a first mixing line connected to the mixing container, a second mixing line connected to the mixing container and the first mixing line, a water line connecting a water source to the first and second mixing lines, a drain conductivity line connected to the first and second mixing lines, a medicament user supply line connecting the medicament user to the first and second mixing lines, and a concentrated medicament supply line connecting the medicament container to the first mixing line, and wherein the pumping of the first quantity of water into the mixing container includes pumping the first quantity of water into the mixing container through the water line and the first mixing line at a pressure below a cracking pressure of a first check valve on the second mixing line while a water line valve on the water line is open, and a drain conductivity line valve on the drain conductivity line, a batch release valve on the medicament user supply line, and a concentrated medicament supply valve on the concentrated medicament supply line are closed.

5. The method of claim 4, wherein the pumping of the fluid in the circular path through the mixing container includes pumping the fluid in the circular path sequentially through the first mixing line, the second mixing line, and the mixing container while the water line valve, the drain conductivity line valve, the batch release valve, and the concentrated medicament supply valve are closed.

6. The method of claim 4, wherein the performing of the first conductivity measurement includes pumping a portion of the first mixed fluid through a conductivity sensor in the drain conductivity line while the drain conductivity line valve is open, and the water line valve, the batch release valve, and the concentrated medicament supply valve are closed.

7. The method of claim 4, wherein the pumping of the final batch of medicament to the medicament user includes pumping the final batch of medicament through the medicament user supply line at a cracking pressure of the first check valve while the batch release valve is open, and the water line valve, the drain conductivity line valve, and the concentrated medicament supply valve are closed, and wherein a second check valve on the medicament user supply line has a cracking pressure that is lower than the cracking pressure of the first check valve.

8. The method of claim 1, wherein the fluid circuit includes a first mixing line connected to the mixing container, a second mixing line connected to the mixing container and the first mixing line, a water line connecting a water source to the first and second mixing lines, a drain conductivity line connected to the first and second mixing lines, a medicament user supply line connecting the medicament user to the first and second mixing lines, and a concentrated medicament supply line connecting the medicament container to the first mixing line, and wherein the pumping of the first quantity of water into the mixing container includes pumping the first quantity of water into the mixing container through the water line and the first mixing line while a water line valve on the water line is open, and a drain conductivity line valve on the drain conductivity line, a batch release valve on the medicament user supply line, and a concentrated medicament supply valve on the concentrated medicament supply line are closed.

9. The method of claim 1, wherein the performing of the first conductivity measurement includes:

pumping a first quantity of the first mixed fluid through a conductivity sensor and measuring, by the conductivity sensor, a conductivity of the first quantity of the first mixed fluid;

in response to the controller determining that a magnitude of the measured conductivity of the first quantity of the first mixed fluid is not greater than a predefined magnitude, pumping a second quantity of the first mixed fluid through the conductivity sensor and measuring, by the conductivity sensor, a conductivity of the second quantity of the first mixed fluid; and in response to the controller determining that the measured conductivity of the second quantity of the first mixed fluid differs from the measured conductivity of the first quantity of the first mixed fluid by less than a predefined range, outputting, by the controller, a measurement based on either one or both of the measured conductivity of the first quantity of the first mixed fluid and the measured conductivity of the second quantity of the first mixed fluid.

10. The method of claim 1, wherein the performing of the first conductivity measurement includes:

pumping a first quantity of the first mixed fluid through a conductivity sensor and measuring, by the conductivity sensor, a conductivity of the first quantity of the first mixed fluid;

in response to the controller determining that a magnitude of the measured conductivity of the first quantity of the first mixed fluid is not greater than a first predefined magnitude, pumping a second quantity of the first mixed fluid through the conductivity sensor and measuring, by the conductivity sensor, a conductivity of the second quantity of the first mixed fluid;

in response to the controller determining that the measured conductivity of the second quantity of the first mixed fluid differs from the measured conductivity of the first quantity of the first mixed fluid by more than a predefined range, further mixing the first mixed fluid through the mixing container and subsequently pumping a third quantity of the first mixed fluid through the conductivity sensor and measuring, by the conductivity sensor, a conductivity of the third quantity of the first mixed fluid;

in response the controller determining that a magnitude of the measured conductivity of the third quantity of the further mixed fluid is not greater than a second predefined magnitude, pumping a fourth quantity of the first mixed fluid through the conductivity sensor and measuring, by the conductivity sensor, a conductivity of the fourth quantity of the first mixed fluid; and in response to the controller determining that the measured conductivity of the fourth quantity of the first mixed fluid differs from the measured conductivity of the third quantity of the first mixed fluid by less than a predefined range, outputting, by the controller, a measurement based on either one or both of the measured conductivity of the third quantity of the first mixed fluid and the measured conductivity of the fourth quantity of the first mixed fluid.

* * * * *